(12) United States Patent
Golovchenko et al.

(10) Patent No.: US 9,815,082 B2
(45) Date of Patent: Nov. 14, 2017

(54) SURFACE WETTING METHOD (71) Applicant: President and Fellows of Harvard College, Cambridge, MA (US)

(72) Inventors: Jene A. Golovchenko, Lexington, MA (US); Bo Lu, Cambridge, MA (US); Aaron T. Kuan, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/775,947

(22) PCT Filed: Mar. 14, 2014

(86) PCT No.: PCT/US2014/029389
§ 371 (c)(1),
(2) Date: Sep. 14, 2015

(87) PCT Pub. No.: WO2014/144818
PCT Pub. Date: Sep. 18, 2014

(65) Prior Publication Data
US 2016/0023239 A1    Jan. 28, 2016

Related U.S. Application Data (60) Provisional application No. 61/790,089, filed on Mar. 15, 2013.

(51) Int. Cl.
*B05D 1/34* (2006.01)
*C25F 3/14* (2006.01)
(Continued)

(52) U.S. Cl.
CPC .......... *B05D 1/34* (2013.01); *B01D 67/0034* (2013.01); *B01D 67/0062* (2013.01); *B01D 67/0065* (2013.01); *B01D 69/02* (2013.01); *C25F 3/00* (2013.01); *C25F 3/14* (2013.01); *B01D 2323/35* (2013.01); *B01D 2325/02* (2013.01)

(58) Field of Classification Search
CPC ..... B01D 167/0034; B01D 69/02; B05D 1/34
See application file for complete search history.

(56) References Cited

PUBLICATIONS

Jose Vincente H. D'Angelo and Artur Z. Franzesconi. Gas-Liquid Solubility of Hydrogen in n-Alcohols (1<4<n) at Pressures from 3.6 MPa to 10 MPa and Temperatures from 298.15 K to 525.15 K. J. Chem. Eng. Datat 2011. 46. pp. 671-674.*

(Continued)

*Primary Examiner* — Dah-Wei D Yuan
*Assistant Examiner* — Kristen A Dagenais
(74) *Attorney, Agent, or Firm* — Theresa A. Lober (57) ABSTRACT

In a method for forming nanopores, two opposing surfaces of a membrane are exposed to an electrically conducting liquid environment. A nanopore nucleation voltage pulse, having a first nucleation pulse amplitude and duration, is applied between the two membrane surfaces, through the liquid environment. After applying the nanopore nucleation voltage pulse, the electrical conductance of the membrane is measured and compared to a first prespecified electrical conductance. Then at least one additional nanopore nucleation voltage pulse is applied between the two membrane surfaces, through the liquid environment, if the measured electrical conductance is no greater than the first prespecified electrical conductance.

20 Claims, 6 Drawing Sheets

(51) Int. Cl.
*B01D 67/00* (2006.01)
*C25F 3/00* (2006.01)
*B01D 69/02* (2006.01)

(56) References Cited

PUBLICATIONS

S. Garaj, W. Hubbard, A. Reina, J. Kong, D. Branton and J.A. Golovchenko. Graphene as a subnanometre trans-electrode membrane. nature vol. 467, Sep. 9, 2010. pp. 190-193 + Methods.*

* cited by examiner

SURFACE WETTING METHOD

CROSS-REFERENCE TO RELATED APPLICATIONS

This application claims the benefit of U.S. Provisional Application No. 61/790,089, filed Mar. 15, 2013, the entirety of which is hereby incorporated by reference.

STATEMENT REGARDING FEDERALLY SPONSORED RESEARCH

This invention was made with Government support under Contract No. 5R01HG003703 awarded by the National Institutes of Health. The Government has certain rights in the invention.

BACKGROUND

This invention relates generally to techniques for producing apertures in thin materials, and more particularly relates to the production of nanopores.

Nano-scale apertures, herein termed nanopores, have attracted much research interest because a nanopore that is provided through the thickness of a nanometrically-thin membrane offers the ability to achieve exceptional resolution for a wide range of molecular sensing and analysis applications, such as DNA sequencing applications, and enables very little flow resistance when employed for, e.g., nano-filtration applications that are in graphene or other very-thin-material membranes, defined here as being of a thickness that is less than about 50 nm, and can be less than 5 nanometers. However, the fabrication of nanopores in such atomically-thin materials, has conventionally be conducted by, e.g., drilling with a focused electron beam. Such processing is tedious, expensive, and can be low-yield because each nanopore must be individually fabricated, e.g., in a high-resolution electron microscope, and because the nanopore size is difficult to tune. In addition, hydrocarbon contamination can be introduced and can accumulate in and around a nanopore during electron beam pore drilling. Such contamination, as well as the inherent surface condition of the material around a nanopore, can render the nanopore hydrophobic, thereby prohibiting wetting of the nanopore. As a result, the reliable, repeatable production of functional nanopores remains a fundamental nanotechnology challenge.

SUMMARY

The many limitations of prior approaches for forming nanopores in nano-scale materials are overcome with a method for forming nanopores that employs a ultra-short electrical pulsing. In one such method, two opposing surfaces of a membrane are exposed to an electrically conducting liquid environment. A nanopore nucleation voltage pulse, having a first nucleation pulse amplitude, is applied between the two membrane surfaces, through the liquid environment. The nanopore nucleation voltage pulse has a pulse duration. After applying the nanopore nucleation voltage pulse, the electrical conductance of the membrane is measured and compared to a first prespecified electrical conductance. Then at least one additional nanopore nucleation voltage pulse is applied between the two membrane surfaces, through the liquid environment, if the measured electrical conductance is no greater than the first prespecified electrical conductance. At least one nanopore diameter tuning voltage pulse, having a tuning pulse voltage amplitude, is applied between the two membrane surfaces, through the liquid environment, if the measured electrical conductance is greater than the first prespecified electrical conductance and no greater than a second prespecified electrical conductance. Each nanopore diameter tuning voltage pulse has a pulse duration.

In a further method for forming a nanopore, two opposing surfaces of a membrane are exposed to an electrically conducting liquid environment, and at least one nanopore nucleation voltage pulse, having a nucleation pulse amplitude and pulse duration, is applied between the two membrane surfaces, through the liquid environment, to produce at the membrane a nanopore nucleation site. After applying the nanopore nucleation voltage pulse, the membrane is processed to produce a preselected nanopore diameter at the nanopore nucleation site.

In a further method for forming a nanopore, two opposing surfaces of a membrane are exposed to an electrically conducting liquid environment. At least two nanopore nucleation voltage pulses, each having a nucleation pulse amplitude and pulse duration, are applied between the two membrane surfaces, through the liquid environment. At least two nanopore diameter tuning voltage pulses, each having a tuning voltage pulse amplitude and pulse duration, are then applied between the two membrane surfaces, through the liquid environment.

Prior to these methods for forming a nanopore, the surface of the membrane can be effectively wetted. In one process for achieving such, a surface, such as a membrane surface, to be wetted is disposed in a local wetting environment; and the local wetting environment is flushed with a flushing gas for a flushing duration sufficient to remove substantially all air from the local wetting environment and replace the air with the flushing gas. Air is prevented from entering back into the local wetting environment. Then a liquid wetting solution is introduced into the local wetting environment. The flushing gas is either 1) chemically reactive with the liquid wetting solution to produce a chemical reaction product that is dissolvable in the liquid wetting solution, or 2) dissolvable in the liquid wetting solution.

These methods enable very efficient, effective, reproducible, and precise nanopore nucleation and tuning, in an environment that maintains the nanopore wetted and free from contamination. The methods are superior for enabling a wide range of nanopore applications in which translocation of a species through a pristine and well-defined nanopore is required. Other features and advantages will be apparent from the following description and accompanying figures, and from the claims.

DETAILED DESCRIPTION

Figure 1:
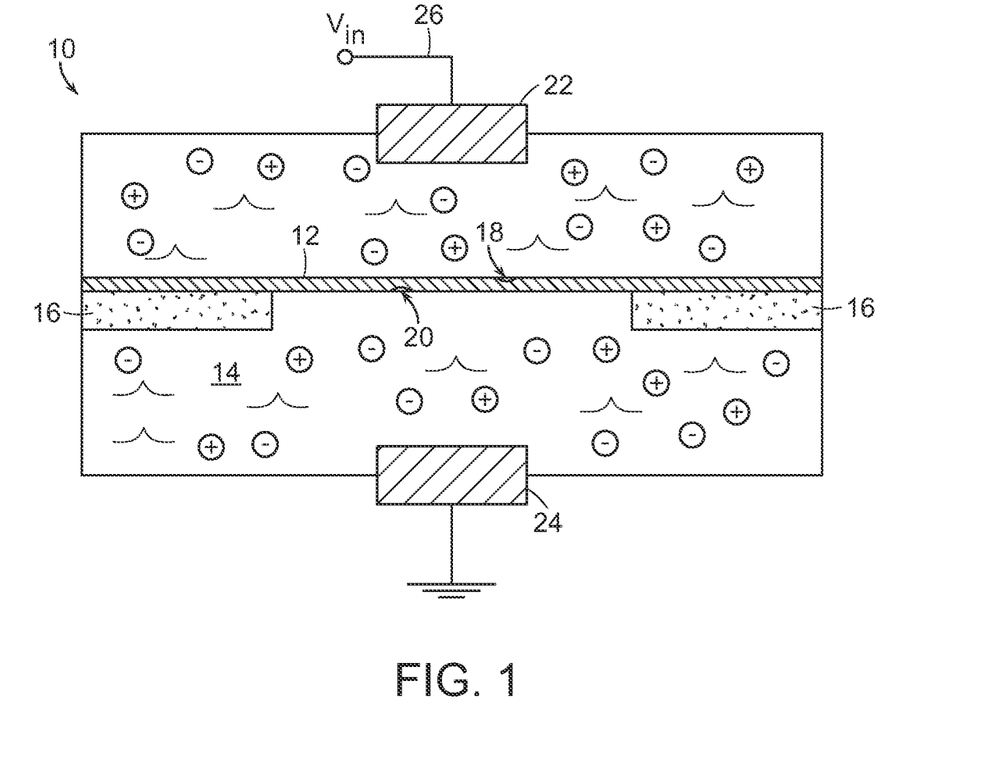
FIG. 1 is a schematic side view of an electrically conducting liquid environment for conducing the nanopore fabrication process.

Referring to FIG. 1, in the nanopore fabrication method provided herein, there is configured an electrically conducting fluid environment 10, with a membrane 12 of a selected material in which one or more nanopores are to be produced being supported in an electrically conducting fluid 14 by a support structure such as a support frame 16. The membrane 12 is a continuous material that is atomically thin, herein defined as a material that includes between about one and about ten atomic layers of material and that is no more than about 50 nm in thickness. Graphene, few-layer graphene, multi-layer graphene, thin graphite, boron nitride, molybdenum disulfide, thin mica, and silicene are examples of atomically-thin materials that can be employed herein. The nanopore fabrication method is particularly well-suited for such atomically-thin materials and in general for membranes having a thickness that is no more than about 5 nm. The membrane 12 can include two or more material layers, including layers of differing material composition. For example the membrane can include a layer of graphene disposed on a layer of boron nitride. No particular material or layers of materials are required. But for any material layer composition, the complete thickness of the membrane is less than about ten atomic layers and/or about 50 nanometers, and preferably less than about 5 nanometers in thickness.

The membrane is mechanically self-supported across the interior extent of the atomically-thin material, and is supported only at its edges by a support frame or other suitable structure 16. The support frame can itself be a self-supported membrane. There is no limitation on the thickness or configuration of the support frame. But the membrane material 12 in which one or more nanopores are to be formed is not mechanically supported at interior regions of the membrane, thereby providing a free-standing region in analogy with a trampoline.

The membrane 12 can optionally include one or more sites 18, 20, at which a material condition, such as a physical defect, is included to effect the nucleation of a nanopore at the site. Such sites can be produced, e.g., by inducing a crystal lattice defect, such as a crystal lattice vacancy, at a selected location in the membrane. For example, ion beam bombardment, electron beam bombardment, UV ozone etch, patterned etching or chemical treatment, or other process can be employed to form one or more sites of a defect or other material condition that encourages nucleation of a nanopore at that site.

As shown in FIG. 1, the membrane of atomically-thin material is arranged in a liquid 14 that includes an electrically conducting solution. In contact with the solution are provided electrically conducting electrodes 22, 24, that are connected in a circuit 26 for applying an electrical potential, $V_{in}$, between the electrodes, across the membrane. The membrane is therefore preferably configured between the electrodes 22, 24, so that the electrodes are on opposite sides of the membrane 12.

Microelectronic substrates, wafers, and other support structures can be employed for holding the membrane material in a suitable configuration for nanopore formation. It can be particularly efficient to produce the membrane in a configuration in which the membrane will be operated for an intended application after nanopore fabrication in the membrane. In one example of such, conventional microelectronic materials are employed to arrange a fabrication environment for a graphene membrane. The graphene membrane material can be synthesized or provided in any suitable manner. For example, single layer graphene can be grown by chemical vapor deposition on a suitable substrate, such as a 25 μm-thick copper foil, at a temperature of, e.g., about 1000° C. The copper is first reduced under flow of hydrogen e.g., 20 sccm, pumped with a scroll pump, for 30 minutes, then methane gas is introduced at a flow rate of 40 sccm as a carbon source. Growth of a graphene layer is conducted under these conditions in about 45 minutes. Exfoliated, epitaxially-grown, or other types of graphene can also be used, and as explained above, other very thin membrane materials, such as multilayer graphene, coated graphene, or boron nitride, can also be used.

Figure 2A:
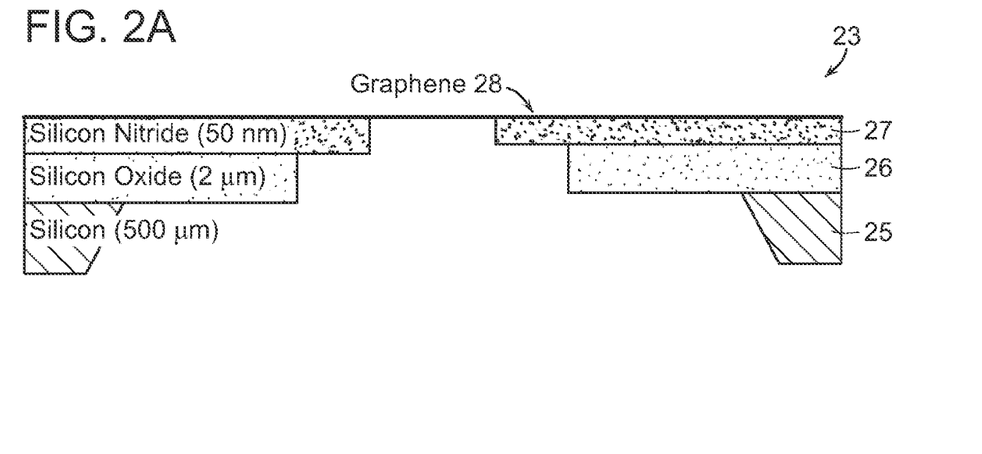
FIGS. 2A and 2B are schematic cross-sectional and top-down views, respectively, of a graphene layer arranged with a support frame structure for nanopore fabrication in the graphene.
Figure 2B:
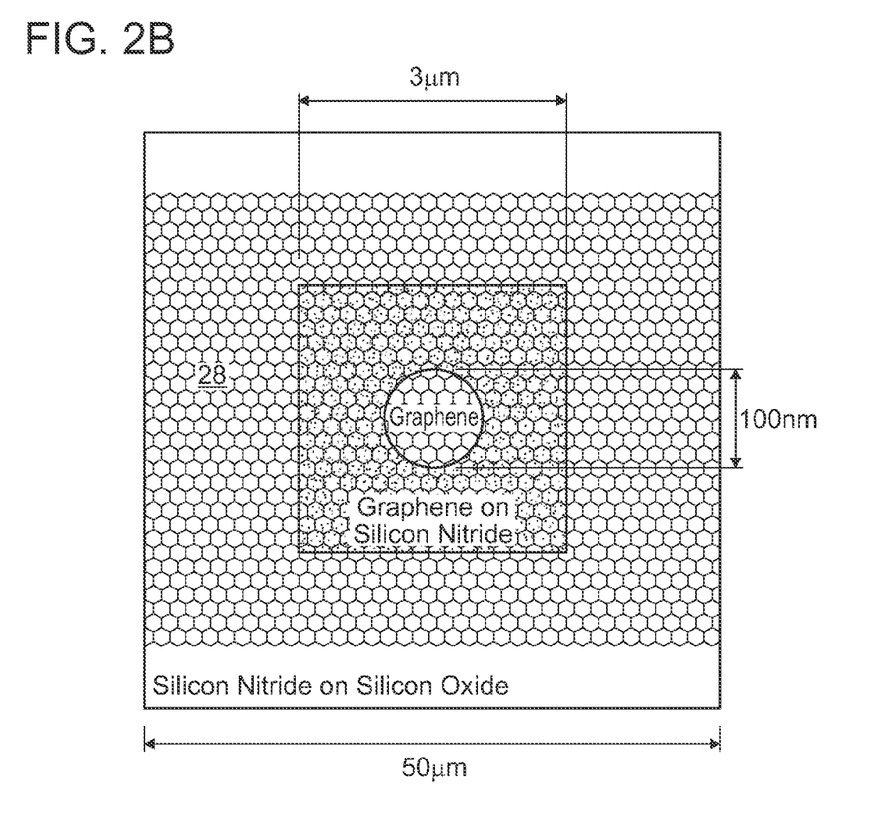

Referring to FIGS. 2A-2B, for many membrane applications, a support frame structure 23 can provide the necessary mechanical arrangement for both nanopore fabrication and subsequent operation. In one example support frame structure 23, there is provided a substrate, such as a conventional silicon wafer of 500 μm in thickness. A membrane support frame is provided on the substrate, formed of, e.g., multiple material layers, such a 50 nm-thick silicon nitride layer atop a 2 μm-thick silicon oxide layer. As shown in the cross-sectional view of FIG. 2A, each of the layers includes an aperture, with the aperture being smallest in the silicon nitride layer and largest in the silicon substrate. As a result, as shown in FIG. 2B, there is provided a silicon nitride membrane having a central aperture, shown as circular in FIG. 2B, the edges of the silicon nitride membrane being supported by a silicon nitride/silicon oxide membrane, the edges of which are support by the silicon substrate. The atomically-thin membrane to be processed is disposed on the surface of the silicon nitride. In one example fabrication process for producing such, the layers of silicon nitride and silicon oxide are blanket coated on the silicon substrate, and with UV lithography and reactive ion etching a window, such as a 650 μm-square window, one per 3 mm die, is formed in the top silicon nitride layer on one side of the wafer. A potassium hydroxide etch is used to etch the silicon down to the oxide layer from the back side of the wafer, releasing a free-standing silicon nitride/silicon dioxide membrane. Focused ion beam milling is used to etch a ~3 μm window through ~90% of the oxide, followed by a hydrogen fluoride etch, which releases a ~3 μm freestanding silicon nitride membrane.

Using a suitable process, such as focused ion beam milling, a circular aperture of between about 100 nm and about 200 nm in diameter is then etched through the silicon nitride membrane. The size of the hole can be varied from a few nanometers to a few microns, above which an atomically-thin material such as graphene will likely not be sufficiently mechanically supported. Other, more scalable methods, such as lithography with reactive ion etching, can be employed rather than sequential ion milling of multiple apertures. The silicon nitride membranes with apertures are preferably cleaned, e.g., with an RCA etch, i.e., ammonium hydroxide, deionized water and 30% hydrogen peroxide in a 5:1:1 volume ratio at 70° C. for 15 minutes, followed by a ammonium fluoride dip, e.g., at room temperature for 1 minute, and finally hydrochloric acid, deionized water, and 30% hydrogen peroxide in a 5:1:1 volume ratio at 70° C. for 15 minutes. With this cleaning step, a selected atomically-thin membrane material can be provided at the site of the support frame structure.

For many atomically-thin materials, such as graphene, it can be required to synthesize the material on a growth host and then transfer the material to a support frame structure. In one example membrane material transfer process, here for graphene, a graphene layer that is synthesized on, e.g., copper foil is transferred to a support frame by way of a support layer. Such a support layer can be formed of any suitable material, e.g., methyl methacrylate (MMA), 6-8% by weight in ethyl lactate, which can be spin-coated on the to surface of a graphene layer as-synthesized on a copper foil, and hard baked for about 5 minutes at 150° C. The copper foil can then be completely etched away, e.g., in an iron chloride bath, by floating the foil on the surface, leaving a graphene region with underlying MMA support layer. The graphene region is then rinsed, with the floating graphene side facing the liquid, preferably in a series of rinses, such as a two rinses in a 1 molar hydrochloric acid bath and three rinses in deionized water. The graphene is left floating on the air-water interface in the last rinse. Then, a piece of the support frame structure wafer, including e.g., 9 or more support frame die, is used to scoop up the graphene region on top of the silicon nitride layer surface, so as to cover the maximum area on the dies. Any water existing between the graphene region and silicon nitride surface can be expelled with a nitrogen gun. It is then preferred to employ a bake, e.g., 95° bake, of the entire structure, to ensure that all water is removed and the graphene is well-bonded, by Van der Waals forces, to the top surface of the silicon nitride layer. Finally, the MMA support layer is removed by rinsing the structure acetone, e.g., at a temperature of about 50° C. for about 30 minutes. The entire structure is then rinsed in ethanol and dried with a critical point dryer. Other methods for preparing a graphene membrane can be employed, and for other atomically-thin materials, other assembly protocols can be required. No particular membrane material preparation is required; but it is preferred that the membrane material be provided in a fixed arrangement on a support frame structure.

With this support structure complete, a fluidic environment including the atomically-thin membrane can be implemented in any suitable manner. One example implementation of a suitable fluidic cell 30 is shown schematically in FIG. 3. The fluidic cell includes two half cells, each formed of a suitable inert material, such as polyetheretherketone (PEEK), forming two microliter volume reservoirs 32, 34. Each reservoir includes suitable fluidic inlets 36 and fluidic outlets 38, injection ports 40 for introducing species into the reservoirs, and electrodes 22, 24 that can be connected in a circuit for applying a voltage between the reservoirs. For example, silver chloride electrodes can be screwed into electrode ports via plastic fittings. Plastic gaskets 42, 44 of suitable material, e.g., molded polydimethylsiloxane (PDMS), are disposed between the half cells, with a support structure including the atomically-thin membrane 12 between the gaskets. The gaskets 42, 44 optionally can include one or more apertures 46 each having a diameter, for example, of between about 10 μm and about 100 μm. The gasket apertures 46 are provided to reduce the area of reservoir liquid in contact with the membrane 12 while providing sufficient liquid contact, in an effort to reduce the device capacitance. In assembly, the two half cells are brought together to encase the membrane and its support structure between the gaskets, fixing the two half cells in place relative to the membrane.

The liquid in the reservoir of each half cell is preferably highly electrically conducting. For many applications, an electrolytic solution including a suitable concentration of electrolyte, such as 1 M-3 M of a common electrolyte like KCl or NaCl, is well-suited for the nanopore fabrication process. Any suitable electrically conducting solution can be employed. The solution can include species, such as molecules, like polymer molecules for a selected nanopore application, such as DNA sequencing or molecular analysis, so that upon nanopore fabrication, the nanopore can be immediately operated in an intended application.

Figure 3:
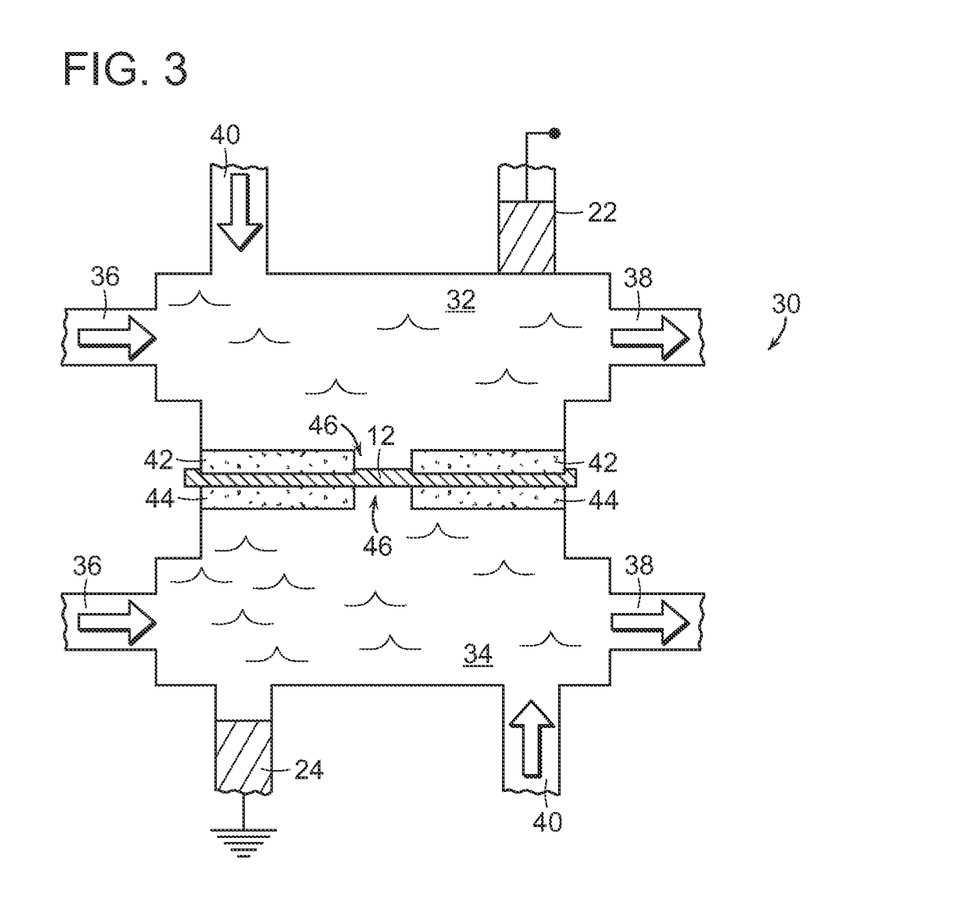
FIG. 3 is a schematic view of a dual chamber flow cell for implementing the liquid environment of FIG. 1 for a nanopore fabrication process.

For many membrane materials, it is found that the characteristics of the membrane material surface can prohibit complete wetting of the membrane surface when the membrane is arranged in the electrically conducting solution. Herein is provided a wetting technique for ensuring that both surfaces of the membrane sufficiently wet in a solution such as an electrolytic solution. In the wetting technique, a local environment in which wetting of a surface is desired, e.g., a fluidic environment vessel such as a flow cell arrangement like that of FIG. 3, is processed with a series of wetting steps that enable substantially complete wetting of the surface with the surface in place in the fluidic environment.

In a first wetting step, the local wetting environment, such as the flow cell, is flushed with a selected flushing gas, such as high-purity carbon dioxide gas, at a sufficient pressure and for a flushing duration that flushes substantially all of the air out of the wetting environment, such as the flow cell. A gas flushing duration of at least a few seconds, and up to about five minutes, can be suitable for most configurations. After the cell is flushed with the selected flushing gas, the flow cell and gas lines are submerged in deionized, degassed water to prevent any air from flowing back into the cell. Then in a second wetting step, while submerged in the deionized water, a selected wetting solution is introduced to the flow cell. The wetting solution is selected in tandem with the selected flushing gas so that upon contact with the flushing gas after introduction into the flow cell, the wetting solution spontaneously reacts with the flushing gas to consume the flushing gas or the flushing gas substantially completely dissolves in the wetting solution.

For example, given a flushing gas of carbon dioxide, there can be employed an aqueous wetting solution including potassium hydroxide (KOH). The KOH in the wetting solution spontaneously reacts with the $CO_2$ flushing gas in a reaction as $2KOH+CO_2 \rightarrow K_2CO_3+H_2O$. The $K_2CO_3$ reaction product including carbonate ($CO_3^{2-}$) ions is highly soluble in water, and immediately dissolves in the KOH solution. After this reaction is initiated, any residual carbon dioxide gas bubbles remaining in the system, and particularly at the surface of the membrane, are consumed by the solution-gas reaction, and the membrane surface thereby completely wets. For example, with a 10 mM KOH solution at 1 atmosphere of pressure and room temperature, the rate of absorption of a $CO_2$ gas bubble is about 0.1 μL/sec·mm$^2$, indicating that any $CO_2$ bubbles smaller than ~1 μl that remain at a membrane surface will dissolve by reaction with KOH in solution within 1 min, thereby quickly achieving complete wetting of the membrane surface.

In this membrane surface wetting procedure, the wetting solution is flowed into the flow cell against the flushing gas pressure, and the flow of flushing gas can then be turned off at a suitable time, such as once the gas-solution reaction is initiated. After a suitable gas-solution reaction duration, e.g., a few minutes, the wetting process is complete and the wetting solution can be replaced with any selected solution for which surface wetting is desired. No air or flushing gas bubbles are introduced, and the membrane surface remains completely wetted. No processing of the membrane surface is required to maintain the wetted condition.

This wetting method is inexpensive, very fast and efficient, and safe, and enables complete wetting of fragile hydrophobic materials, such as graphene membranes, that can be physically destroyed by conventional hydrophilic treatments. This wetting procedure enables the wetting of graphene surfaces and graphene nanopores with a yield of >95%. The wetting method is applicable to any micro-scale or nano-scale system in which surface wetting is required.

This surface wetting method is not limited to the $CO_2$ flushing gas and KOH aqueous solutions described above. Any flushing gas-wetting solution pair can be employed in which the flushing gas either reacts with the wetting solution to form a soluble reaction product or itself dissolves in the wetting solution. For example, the $CO_2$ flushing gas can be employed with any wetting solution that is pH basic, such as NaOH or $NH_4OH$. Similarly, $Cl_2$ flushing gas can be employed with a basic wetting solution such as KOH, NaOH, or $NH_4OH$, whereby reaction product $ClO^-$ ions can be dissolved in solution upon reaction between the $Cl_2$ and the solution. Any suitable flushing gas can be employed, including, e.g., ammonia gas or other selected gas, along with a selected companion wetting solution that operates to remove flushing gas.

Other surface wetting techniques can be employed; no particular wetting process is required. It is, however, preferable that both sides of the membrane surface be fully wetted and in full contact with the electrically conducting solution. Whatever wetting process is employed, it is preferable to confirm the compatibility of the process gases and liquids with a membrane material under consideration.

Once the membrane is wetted in the liquid flow cell solution with a selected electrically conducting liquid, there is initiated the procedure of nucleation of a nanopore or nanopores in the membrane. In a first step nucleation, the electrical leakage conductance of the membrane is measured. The leakage conductance can be measured with any suitable technique. In one example technique, a voltage ramp of suitable amplitude, such as −150 mV to +150 mV over 10 seconds, can be imposed across the membrane at the flow cell electrodes, e.g., using a signal generator, and the resulting current through the system, between the electrodes across the membrane, is measured, e.g., with a current amplifier connected in series with the membrane. It is preferred that the voltage amplitude applied in measuring leakage conductance be relatively low, e.g., no greater than about ±300 mV, to ensure that the measurement does not disrupt the membrane surface.

Figure 4A:
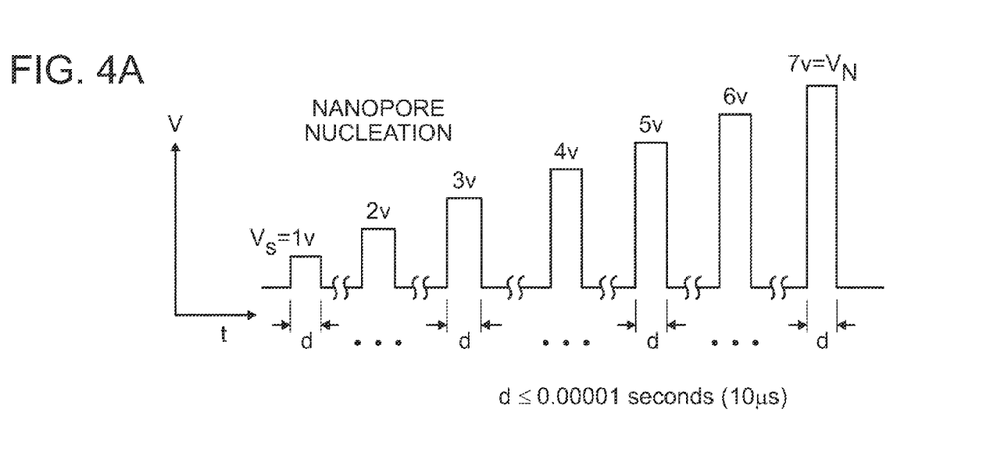
FIG. 4A is plot of nucleation voltage pulse duration for a sequence of nucleation voltage pulses applied in the liquid environment of FIG. 1 for nucleating a nanopore in an atomically-thin membrane.

Referring to FIG. 4A, once the leakage conductance is determined, then one or more nanopores are nucleated in the membrane by applying at least one ultra-short nucleation voltage pulse, and for many applications, preferably a sequence of ultra-short nucleation voltage pulses, between the electrodes in the solution. Each nucleation voltage pulse has a pulse duration, d, that can be the same duration as that of other nucleation pulses in the pulse sequence, or that can be a distinct pulse duration. The duration of each nucleation voltage pulse is no greater than about 0.00001 seconds, or $10 \times 10^{-6}$ seconds, and for many applications, is preferably no greater than about $500 \times 10^{-9}$ seconds and for some applications is preferably no greater than $250 \times 10^{-9}$ seconds. The duration of each nucleation voltage pulse is at least about $100 \times 10^{-9}$ seconds to accommodate RC charging in the system across the membrane. With these requirements, each nucleation voltage pulse duration is at least about 100,000 times shorter than one second.

The amplitude of the first nucleation voltage pulse in a sequence of ultra-short voltage pulses is set at a starting voltage, $V_s$, and thereafter, the voltage of each subsequent nucleation voltage pulse can be increased or can repeat a previous voltage level. The first voltage pulse is set at a voltage below a minimum voltage that is expected for nucleating a nanopore, e.g., 1 V, and the voltage amplitude of each subsequent pulse can be incrementally increased by a relatively small value, e.g., 1 V or less, such as 100 mV. Between each nucleation voltage pulse application, there is a pause in nucleation voltage pulse application of at least about the duration of the RC time constant for the system, e.g., $10 \times 10^{-9}$ seconds.

After a first nucleation voltage pulse and any subsequent pulses that are included, it can be preferred to measure the conductance of the membrane to determine if a nanopore has nucleated in the membrane. If after a nucleation voltage pulse the conductance of the membrane is found to have increased over the leakage conductance measured earlier, then the nucleation of a nanopore is indicated; for example, if the measured conductance is found to have increased appreciably, e.g., to at least about, e.g. 1 nS to 10 nS, here for an example of a liquid 1M KCl solution, then nanopore nucleation is confirmed. The site of a nucleated nanopore is physically characterized by an extent that can be less than 1 nm. For many materials, this nucleated nanopore extends through the thickness of the membrane, but may not extend through the membrane thickness for all materials. Once nanopore nucleation is confirmed, no additional nanopore nucleation voltage pulses are required. This nanopore nucleation confirmation can occur after one nanopore nucleation voltage pulse is applied or after two or more nanopore nucleation voltage pulses are applied.

In making a membrane conductance measurement to confirm nanopore nucleation, it can be preferred to employ a relatively low-amplitude pulse of voltage, e.g., a voltage less than about ±300 mV, to ensure that the conductance measurement does not alter any nanopore that may have nucleated during a previous voltage pulse. At such low voltages, no damage is done to the membrane or nanopore, so measurements 1 sec or longer can be used to accurately measure conductance.

Once it is confirmed that one or more nanopores have nucleated in the membrane, then if desired, the diameter of the nanopore can be enlarged by removal of material from the membrane at edges of the nucleated nanopore. Such nanopore diameter enlargement is not required, and may not be necessary for a given application, but for many applications, can be employed for tuning the nucleated nanopore diameter. Any suitable process can be employed to enlarge a nanopore diameter. For example, membrane etching, by liquid, vapor, plasma, or other species, can be employed to remove membrane material from nanopore edges. The nanopore diameter can be tuned to a prespecified selected nanopore diameter that is desired for the nucleated nanopore. No particular nanopore diameter tuning method is required and indeed, as just explained, for some applications nanopore nucleation can be sufficient.

In one elegantly convenient technique nanopore diameter tuning technique, referring back to FIG. 1, a sequence of ultra-short voltage pulses is applied between the electrodes in solution in the manner described above for nucleating a nanopore. With this technique, the nanopore diameter can be tuned to an a priori prespecified nanopore diameter, as described in detail below, or can be enlarged in an open loop fashion. In either scenario, there is applied at least one ultra-short tuning voltage pulse, or for many applications, a sequence of ultra-short tuning voltage pulses.

Figure 4B:
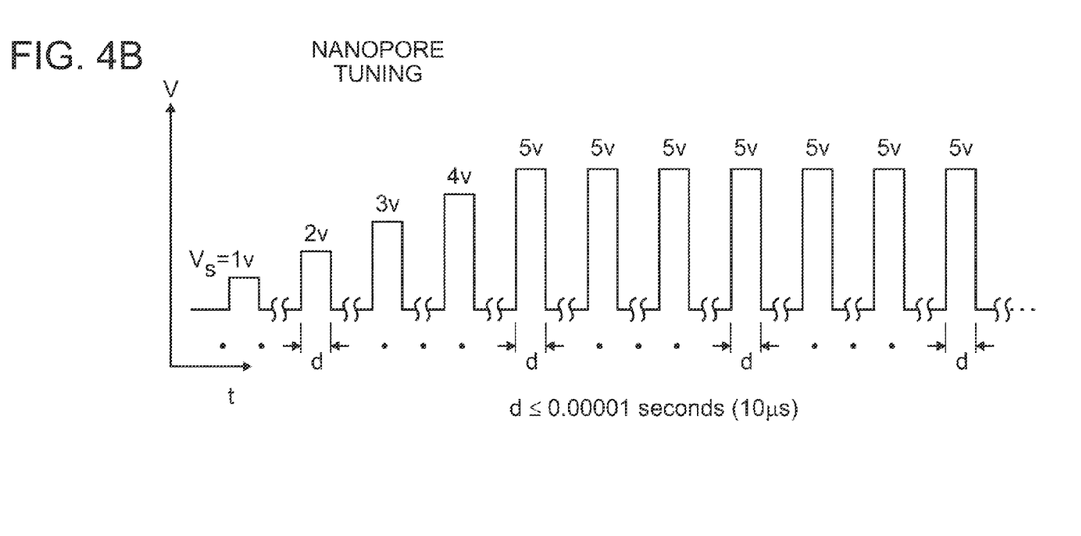
FIG. 4B is plot of tuning voltage pulse duration for a sequence of tuning voltage pulses applied in the liquid environment of FIG. 1 for enlarging a nanopore that has been nucleated in an atomically-thin membrane.

Referring to FIG. 4B, in such a sequence of tuning voltage pulses, the first tuning voltage pulse has a pulse amplitude, $V_s$, that is similar to the starting amplitude of the first nucleation voltage pulse for nucleating a nanopore. Each subsequent tuning voltage pulse amplitude can be greater than that of previous pulses or can provide consecutive pulses of equal voltage amplitude. Each tuning voltage pulse has a pulse duration, d, that can be the same duration as that of other tuning voltage pulses in the pulse sequence, or that can be a distinct pulse duration. The duration of each tuning voltage pulse can be set to any suitable value. For many applications, it can be preferred that a tuning voltage pulse duration that is no greater than about 0.00001 seconds, or $10 \times 10^{-6}$ seconds, and for many applications, is preferably no greater than about $500 \times 10^{-9}$ seconds. The duration of each tuning voltage pulse is at least about $100 \times 10^{-9}$ seconds to accommodate RC charging in the system across the membrane. With these requirements, each tuning voltage pulse duration is at least about 100,000 times shorter than one second. Each tuning pulse duration can be the same, or can be shorter than prior pulses as a desired nanopore diameter is neared. Each nanopore nucleation pulse and each nanopore tuning pulse can be of the same duration.

It is discovered in the nanopore fabrication process herein that the duration of the voltage pulses for both nanopore diameter enlargement as well as for nanopore nucleation are preferably shorter than about 0.00001 seconds, or $10 \times 10^{-6}$ seconds, and for many applications, the pulse duration is preferably shorter than about $500 \times 10^{-9}$ seconds or $250 \times 10^{-9}$ seconds. Any voltage pulse duration longer than about 0.00001 seconds can damage the atomically-thin membrane, and a voltage application of as long as one second can be expected to locally destroy the atomically-thin membrane. A continuous voltage application, even when ramped in voltage amplitude, cannot be applied. Instead, it is discovered that to preserve the mechanical integrity of the atomically-thin membrane, voltage pulses having a duration that is at least 100,000 times shorter than one second are required.

It is discovered herein that nanopores smaller than 1 nm in diameter can be created and controllably enlarged in atomically thin membranes with subnanometer precision by applying an electric field that is not localized on the nanometer scale. Indeed, continuous voltage application destroys the mechanical integrity of atomically-thin membranes so quickly that feedback measurement of the pore current cannot be used to control pore size on the nanometer scale. Only the application of voltage pulses having a pulse duration within a very small pulse duration range that is between the RC charging time of the membrane, which is about $10^{-7}$ seconds, and the time scale of membrane destruction, which can be $10^{-6}$ seconds or less, allows one to arrest this violent process in a way that affords precise control of pore size on the nanoscale.

The nanopore diameter can be precisely tuned to a prespecified diameter by calibrating nanopore sizes with corresponding membrane electrical conductance values for a specified membrane material and electrolytic solution. Here the conductance of a given membrane in a selected electrolytic solution can be calculated as a function of nanopore size in the membrane by, e.g., finite element simulation and analysis, or by analytical approximation. Alternatively, nanopores can be physically formed by, e.g., electron beam drilling, in a selected membrane material and the conductance of the nanopores experimentally measured as a function of nanopore size in a selected electrolyte solution. For many atomically-thin membranes, such as single layer graphene, the conductance of the membrane scales linearly with nanopore diameter. For example, in a 1 M KCl solution, the nanopore diameter in Angstroms is approximately equal to the conductance in nanoSiemens.

With a known correlation between membrane conductance and nanopore diameter, the nanopore tuning method can be precisely controlled for a calibrated membrane material and electrolytic solution. After each tuning voltage pulse applied to a nucleated nanopore, a measurement voltage pulse can be applied to measure the conductance of the membrane for assessing the extent of the nanopore. The measurement voltage pulse is preferably of a relatively low voltage amplitude, e.g., about 300 mV, applied in the manner described above, so as to not affect the state of the nanopore. With such a measurement pulse, the membrane conductance can be measured for determination of nanopore diameter.

After a membrane conductance measurement, a subsequent nanopore diameter tuning voltage pulse can be applied to the electrodes, with the subsequent tuning pulse providing increased voltage amplitude or constant voltage amplitude. The voltage pulse amplitude can be increased from one tuning voltage pulse to the next until an increase in membrane conductance is observed, indicating that the nucleated pore diameter has increased. Once it is determined that the nucleated pore extent is increasing, the tuning voltage pulse amplitude can be held constant for subsequent tuning voltage pulses, in the manner shown in FIG. 3B for 5 V-amplitude voltage pulses. As the nanopore enlarges, it can be preferred to vary the pulse duration, d, to increase the precision of control over nanopore growth. The tuning pulse duration, d, can therefore be decreased over the pulse sequence as the nanopore diameter increases.

It is discovered in the nanopore fabrication process herein that if a membrane conductance measurement is employed to determine the conditions of nanopore nucleation and/or enlargement, such a membrane conductance measurement must be made between applied voltage pulses. It is not feasible to monitor the system conductance while a voltage pulse is being applied with the intent of ending the voltage pulse when a desired nanopore diameter is attained. The time scale in which a nanopore enlarges in the nanometer range is on the order of the RC charging time of the membrane. During the duration of the RC charging time, the current through a nanopore cannot be measured accurately because it is dominated by the capacitive current originating from the voltage pulse. As a result, the current through the nanopore, and consequently, the nanopore size, cannot be measured before it has grown far beyond the desired size. It is therefore preferred that each ultra-short voltage pulse be applied without monitoring the system conductance during the voltage pulse application, after which the nanopore conductance can measured with a low voltage bias, and can be safely applied for relatively long times without destroying the membrane.

The nanopore tuning process can be fully calibrated for a selected membrane material and other system parameters and then conducted in an open-loop fashion without conductance measurement during the process. For example, one or more nanopore nucleation voltage pulses can be applied with preselected pulse amplitude and duration that are known to produce nanopore nucleation, and then a selected process can be undertaken to tune the diameter of the nucleated nanopore. For example, one or more nanopore tuning voltage pulses can be applied with preselected pulse amplitude and duration that are known to produce a pre-specified nanopore diameter. This process can include, e.g., one nanopore nucleation voltage pulse and one nanopore tuning voltage pulse, with each pulse prespecified for ultimately producing a selected nanopore diameter.

As explained above, any suitable process can be employed to enlarge a nanopore diameter once nanopore nucleation is confirmed. Application of voltage pulses in the manner described above can be particularly efficient and effective, but other processes can be employed. For example, chemical species can be introduced to the liquid environment to chemically enlarge a nucleated nanopore. In one example of such, potassium permanganate in sulfuric acid solution is introduced into a liquid environment in which a graphene membrane and nanopore are disposed to react with the graphene nanopore walls and enlarge the nanopore in the graphene. In other examples, the temperature of the liquid environment can be controlled to tune a nanopore size. For example, the liquid can be heated to enlarge a nanopore. In addition, there can be employed a range of electrical processes that tune a nanopore diameter, e.g., to enlarge a nanopore.

Beyond nanopore tuning, after nanopore nucleation and/or diameter tuning the membrane can be further processed for any particular requirements. For example, the membrane and/or nanopore can be coated with materials by chemical or physical deposition, such as atomic layer deposition. Such material coating can include microelectronic materials, such as electrically insulating materials, and can include molecules, such as lipid molecules, employed for a selected application. These examples demonstrate that once a nanopore is nucleated in a membrane by one or more ultra-short voltage pulses, a wide range of processes can be employed to tune the nanopore diameter and to customize the local materials and structure at the site of the nanopore.

With these fabrication processes and surface wetting technique, a nanopore is precisely formed in-solution and remains wetted in solution at the conclusion of the nanopore nucleation and tuning steps, and thus can immediately be used for solution measurements without a need for removal from the solution environment. The surface of the membrane can be maintained in pristine condition, without contamination that could occur by ambient exposure out of the solution. Thereby are enabled highly precise nanopore applications, such as DNA translocation through the nanopore.

Example I

Nanopore Nucleation and Enlargement in a Graphene Membrane

Figure 5:
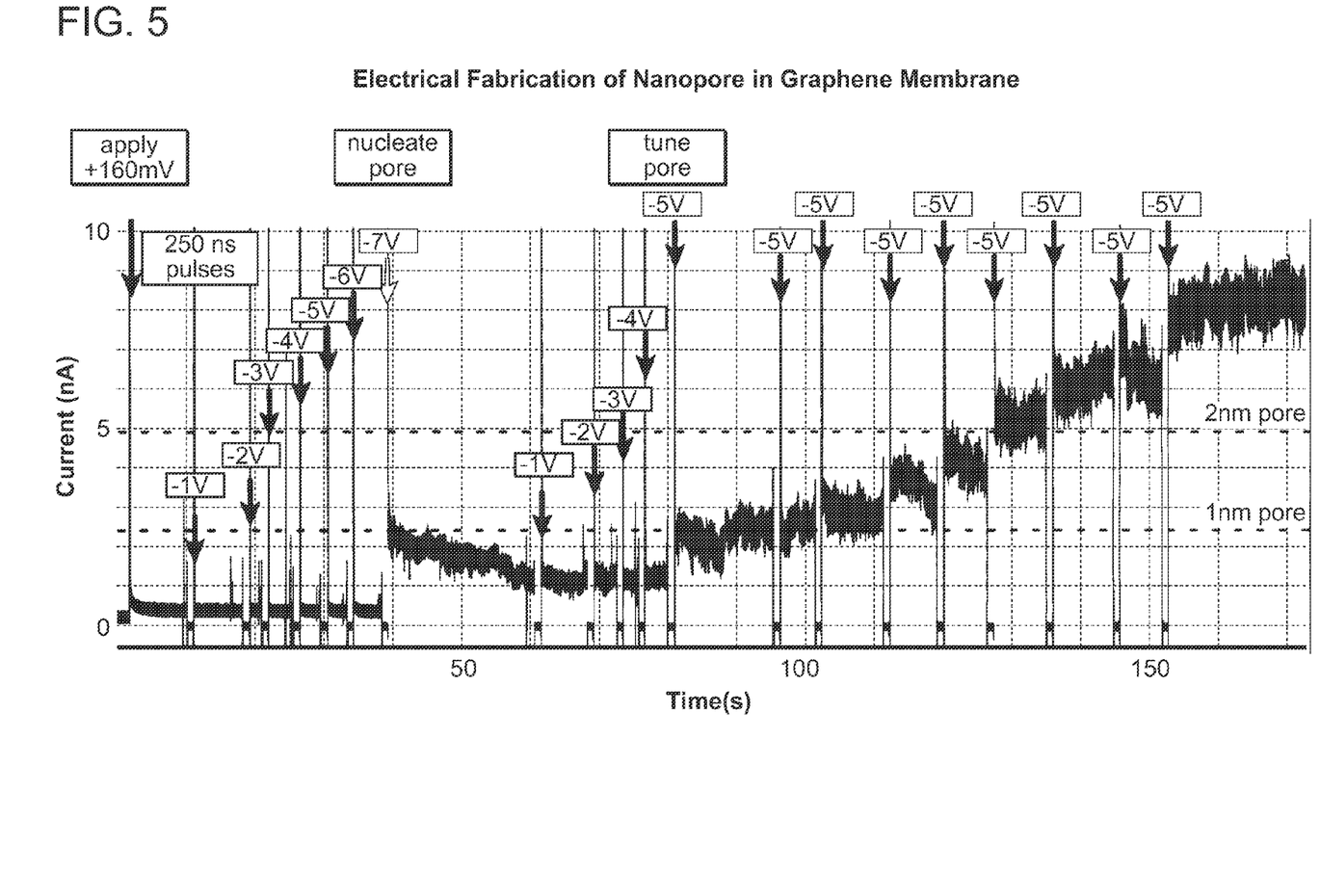
FIG. 5 is plot of nucleation voltage pulse duration and tuning voltage pulse duration for a sequence of nucleation and tuning voltage pulses that were experimentally applied to a graphene membrane in the liquid environment of FIG. 1 for nucleating and enlarging a nanopore in a graphene membrane.

A graphene membrane was assembled with a support frame structure of silicon nitride, silicon oxide, and a silicon substrate, as shown in FIGS. 2A-2B. The support structure was arranged in a flow cell like that of FIG. 3, configured with 3 M KCl solution at room temperature. A nanopore nucleation and tuning process was conducted in the manner described above. FIG. 5 is a plot of the voltage amplitude of each applied voltage and the current that was measured between each voltage pulse. Each voltage pulse, both in the nucleation voltage sequence and the tuning voltage sequence, was $250 \times 10^{-9}$ seconds in duration.

A low voltage bias of 160 mV was applied across the membrane for conductance measurement, and conductance was measured using an Axopatch 200B low noise current amplifier. An Arduino Uno R3 board was programmed to allow manual control of the nanopore fabrication process. In response to a button manually pressed on the Arduino Uno, the membrane was disconnected from the Axopatch current amplifier and connected to an HP 8110A pulse generator by way of a mechanical relay (Panasonic TN2-5V). After a delay of 1 second, the Arduino board triggered the pulse generator, which applied a pulse of 250 ns with manually-specified voltage amplitude, and reconnected the membrane to the low noise current amplifier to monitor the nanopore size. These steps were repeated several times as indicated in the diagram.

Figure 6:
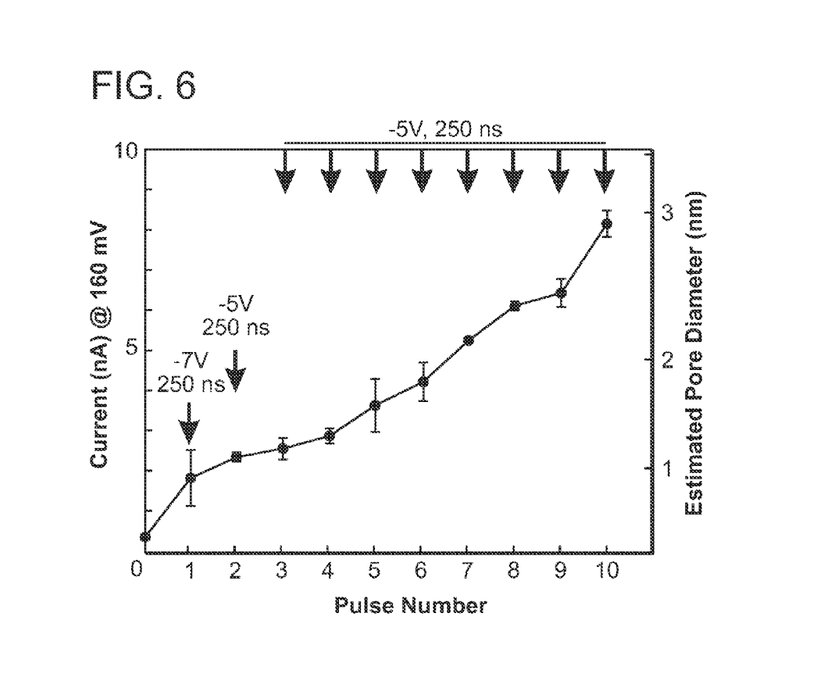
FIG. 6 is a plot of nanopore diameter calculated from electrical current for the nanopore nucleation and enlarging process depicted in the plot of FIG. 5, shown as a function of applied voltage pulse number.

As shown in the plot of FIG. 5, after an application of seven nucleation voltage pulses, starting at 1 V in amplitude and increasing to 7 V in amplitude, there was nucleated a nanopore, as evidenced by a jump in measured current. A sequence of tuning voltage pulses was then initiated, beginning again with a starting voltage of 1 V. After application of five tuning voltage pulses, increasing in amplitude from 1 V to 5 V, the nanopore began to enlarge, as evidenced by a jump in measured current. After the measured jump in current, the tuning voltage pulse amplitude was held constant at 5 V and the sequence of tuning voltage pulses was continued. As shown in the plot, the measured conductance continued to increase as the tuning voltage pulse sequence continued, indicating an increase in nanopore diameter. FIG. 6 is a plot of calculated nanopore diameter as a function of voltage pulse number, including nucleation voltage pulses and tuning voltage pulses.

In making observations of a nanopore in an atomically-thin material, it is found that imaging of a nanopore can be difficult because the image contrast can be poor, particularly for single-layer graphene. A transmission electron microscope (TEM) is necessary, and aberration corrected microscope at low energies (80 kV) is very helpful. In one process for successfully imaging a nanopore in a graphene membrane, the graphene membrane as-arranged on a support structure is first carefully removed from a flow cell and quickly immersed in deionized water. The membrane and support structure should not be allowed to dry in air. At a time for imaging the nanopore, the membrane and support structure should be dried with a critical point dryer. Contaminants can cover a nanopore during the drying process and exposure to ambient air, making imaging unsuccessful. In addition, imaging with a beam having an energy above about 200 kV can gradually induce defects in an atomically-thin material such as single-layer graphene. Therefore, it is preferred to very quickly obtain an image. Clean graphene often looks similar to vacuum, so interpretation of the images is also difficult.

The conductance measurement data of FIG. 5 demonstrate that with nucleation and tuning voltage pulses of no more than $250 \times 10^{-9}$ seconds in duration, a nanopore is nucleated in a graphene membrane and the nanopore diameter is controllably and precisely enlarged, pulse-by-pulse, to a desired diameter, in this experimental example, 3 nm. The nanopore nucleation is distinctly indicated by measured conductance values after each nucleation voltage pulse, and nanopore diameter increase is clearly correlated to measured conductance values after each tuning voltage pulse. The nanopore fabrication method is demonstrated to reliably produce nanopores while maintaining the mechanical integrity of the membrane material.

Example II

DNA Translocation Through a Nanopore Fabricated in a Graphene Membrane

The nanopore of Example I having a diameter of 3.5 nm was positioned in the flow cell of FIG. 3 in a 3 M KCl solution. −10 kbp dsDNA was dissolved in the electrolyte solution of 3 M KCl at a concentration of 4 ng/μL. 45 μL of the solution including DNA was injected into the injection port of the fluidic cell into the half-cell on the top side of the structure, that being the side having the graphene layer fully exposed on top of the silicon nitride/silicon oxide support structure, as opposed to the underside, on which the surface of the lower silicon substrate was exposed. Using a patch-clamp amplifier (Axopatch 200B), a −160 mV bias was applied to the electrode on the graphene layer side of the structure. This voltage bias electrophoretically drove the DNA molecules in the solution to translocate through the nanopore from the graphene layer side of the structure to the silicon substrate side of the structure. During the voltage application, the ionic current through the nanopore was monitored using the patch-clamp amplifier. DNA translocations were detected as transient current blockades in the measured ionic current.

Figure 7:
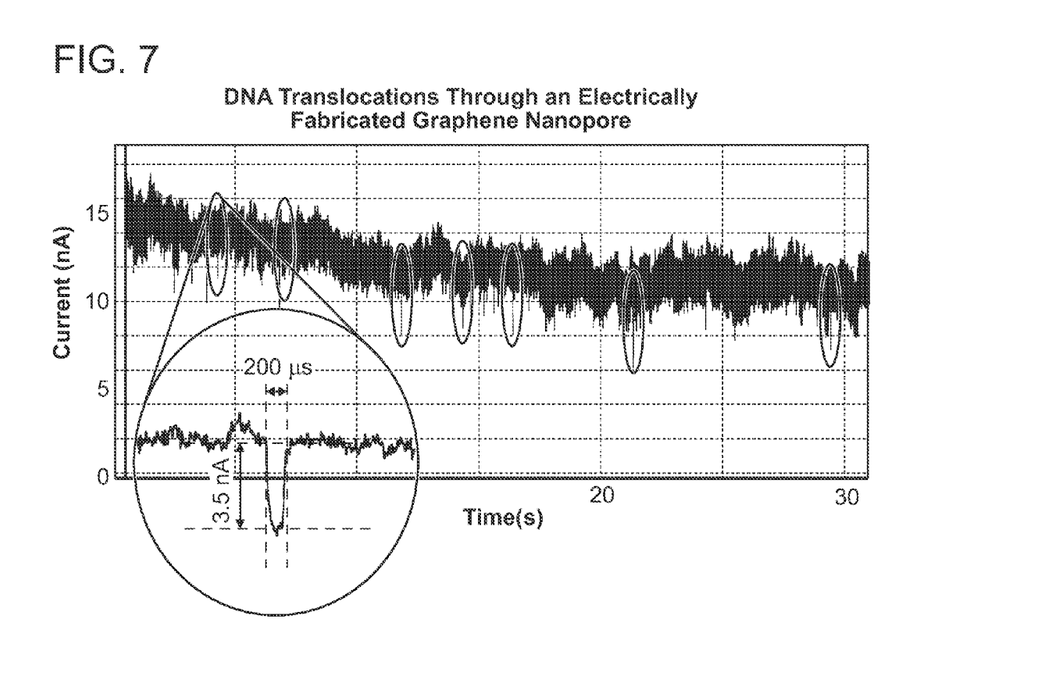
FIG. 7 is a plot of measured electrical current as a function of time during an experimental process of translocating DNA through a nanopore fabricated by the nanopore nucleation and enlarging process depicted in the plot of FIG. 5.

As shown in the plot of FIG. 7, each measured current blockade consisted of a drop in measured current, for example, a current drop of about 3.5 nA, over a duration of about $200 \times 10^{-6}$ seconds. These conditions directly correspond to a blockage of ionic current due to the presence of the DNA molecule threaded through the nanopore. This DNA translocation through the nanopore was conducted over several minutes. This demonstrates that nanopores fabricated by ultra-short voltage pulse in the methodology herein are sufficiently robust and well-defined to enable DNA translocation through the nanopore over an extended duration of operation.

The examples and description above demonstrate the precision and high level of dimensional control that is achieved with the nanopore fabrication process provided herein, providing repeatability and elegant simplicity in its implementation. While the process description has presented a scenario in the fabrication of a single nanopore, the process is easily configured for scalability. As explained above, a membrane material can be provided with an array of surface sites each having a condition, or defect, that encourages nanopore nucleation at the site, whereby an array of nanopores can be fabricated simultaneously. Alternatively, there can be employed arrays of electrodes, or electrodes that can scan across the surface of the membrane material, as electrical pulses are applied to the electrodes, to fabricate a plurality of nanopores in the material, e.g., as a prespecified array of nanopores. Such arrays of nanopores can be particularly advantageous for, e.g., nanofiltration applications.

The nanopore fabrication process can be employed with any suitable atomically-thin material or layers of material that together are less than about ten atomic layers thick, or less than about 50 nanometers-thick, less than about 10 nanometers thick, or even less than about 5 nanometers-thick. The nanopore fabrication process can be conducted in the presence of any selected species in the liquid environment of the nanopore formation, including chemically reactive species and species such as polymer molecules that are to be examined after nanopore formation. Further, a selected one or more chemical species can be included in the liquid environment, during nanopore formation, for example, to modify the edges of the nanopore during nanopore formation or to enlarge the nanopore, as well as to modify or react with the membrane material. Thus, the nanopore fabrication process is amenable to extensive adaption for customizing a nanopore and its environment for a selected application.

It is recognized that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A method for wetting a surface comprising:
disposing a surface to be wetted in a local wetting environment;
flushing the local wetting environment with a flushing gas for a flushing duration that replaces air in the wetting environment with the flushing gas;
preventing air from entering back into the local wetting environment; and
introducing a liquid wetting solution into the local wetting environment while the flushing gas is in the wetting environment, the flushing gas having at least one condition selected from the group consisting of 1) being chemically reactive with the liquid wetting solution to produce a chemical reaction product that is dissolvable in the liquid wetting solution and 2) being dissolvable in the liquid wetting solution.

2. The method of claim 1 wherein disposing the surface to be wetted in a local wetting environment comprises disposing a membrane, having two opposing surfaces to be wetted, in the local wetting environment.

3. The method of claim 1 wherein disposing the surface to be wetted in a local wetting environment comprises disposing a structure, have a surface to be wetted, in a liquid flow cell.

4. The method of claim 3 wherein disposing the structure in a liquid flow cell comprises disposing the structure in a liquid flow cell that contains no liquid.

5. The method of claim 1 wherein flushing the local wetting environment with a flushing gas comprises flowing the flushing gas at a flow pressure that flushes all air from the local wetting environment.

6. The method of claim 1 wherein the local wetting environment is a vessel.

7. The method of claim 1 wherein the local wetting environment is a vessel having at least one inlet port, and wherein preventing air from entering hack into the local wetting environment comprises submerging the vessel in a liquid while flowing the flushing gas into the vessel.

8. The method of claim 1 wherein introducing a liquid wetting solution into the local wetting environment comprises flowing the liquid wetting solution into the local wetting environment while flowing the flushing gas into the local wetting environment.

9. The method of claim 1 wherein the flushing gas comprises carbon dioxide.

10. The method of claim 1 wherein the flushing gas comprises chlorine gas.

11. The method of claim 1 wherein the flushing gas is selected from the group consisting of carbon dioxide gas, ammonia gas, and chlorine gas, and wherein the wetting solution is a pH basic liquid.

12. The method of claim 1 wherein the flushing gas is chemically reactive with the liquid wetting solution to produce a chemical reaction product comprising electrically charged ions that are dissolvable in the liquid wetting solution.

13. The method of claim 1 wherein the flushing gas is selected from the group consisting of carbon dioxide and chlorine gas, and wherein the wetting solution is selected from the group consisting of KOH, NaOH, and $NH_4OH$.

14. The method of claim 1 wherein the surface to be wetted comprises a nanopore surface through a thickness of a membrane.

15. The method of claim 1 wherein the surface to be wetted comprises opposing surfaces of an atomically-thin membrane having no more than 10 atomic layers in thickness.

16. The method of claim 1 wherein surface to be wetted comprises a graphene surface.

17. The method of claim 1 wherein introducing a liquid wetting solution into the local wetting environment comprises filling the local wetting environment with the liquid wetting solution.

18. The method of claim 1 further comprising replacing the wetting solution in the local wetting environment with a selected liquid solution whereby the surface to be wetted is wetted by the selected liquid solution as the selected liquid solution replaces the wetting solution.

19. The method of claim 18 wherein the selected liquid solution replacing the wetting solution is an electrolytic solution.

20. The method of claim 19 wherein the electrolytic solution includes polymer molecules.

* * * * *